United States Patent
Kwak et al.

(10) Patent No.: US 12,041,938 B2
(45) Date of Patent: Jul. 23, 2024

(54) COMPOSITION FOR PROMOTING GROWTH OF EFFECTIVE MICROORGANISM AND CONTROLLING PLANT DISEASE USING PREBIOTICS, AND USE THEREOF

(71) Applicant: INDUSTRY-ACADEMIC COOPERATION FOUNDATION GYEONGSANG NATIONAL UNIVERSITY, Gyeongsangnam-do (KR)

(72) Inventors: Youn-Sig Kwak, Gyeongsangnam-do (KR); Da-Ran Kim, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 552 days.

(21) Appl. No.: 17/311,771

(22) PCT Filed: Dec. 6, 2019

(86) PCT No.: PCT/KR2019/017238
§ 371 (c)(1),
(2) Date: Jun. 8, 2021

(87) PCT Pub. No.: WO2020/130444
PCT Pub. Date: Jun. 25, 2020

(65) Prior Publication Data
US 2022/0110331 A1    Apr. 14, 2022

(30) Foreign Application Priority Data

Dec. 21, 2018  (KR) .................. 10-2018-0166923
Oct. 23, 2019  (KR) .................. 10-2019-0131906

(51) Int. Cl.
| | |
|---|---|
| *A01N 63/28* | (2020.01) |
| *A01N 33/08* | (2006.01) |
| *C12N 1/20* | (2006.01) |
| *C12N 1/38* | (2006.01) |
| *C12R 1/465* | (2006.01) |

(52) U.S. Cl.
CPC ............ *A01N 63/28* (2020.01); *A01N 33/08* (2013.01); *C12N 1/205* (2021.05); *C12N 1/38* (2013.01); *C12R 2001/465* (2021.05)

(58) Field of Classification Search
None
See application file for complete search history.

(56) References Cited

FOREIGN PATENT DOCUMENTS

| | | |
|---|---|---|
| JP | 2870015 B2 | 3/1999 |
| KR | 10-2015-0009680 A | 1/2015 |
| KR | 10-2015-0126666 A | 11/2015 |
| KR | 10-1626387 B1 | 6/2016 |
| KR | 10-2017-0000094 A | 1/2017 |
| KR | 10-2017-0000514 A | 1/2017 |
| KR | 10-1695918 B1 | 1/2017 |
| KR | 10-2018-0112255 A | 10/2018 |

OTHER PUBLICATIONS

English Translation KR-2018-012255-A (Year: 2018).*
English Translation KR-2017-0000514-A (Year: 2017).*
Alam et al., "Streptomyces: The biofactory of secondary metabolites." Frontiers in Microbiology. 13:968053. (Year: 2022).*
Niu et al. "Specialised metabolites regulating antibiotic biosynthesis in Streptomyces spp." FEMS Microbiology Reviews, fuw012, 40, 2016, 554-573. (Year: 2016).*
"BD Difco Dehydrated Culture Media: ISP Medium 2" downloaded from fisherscientific Apr. 17, 2024. <https://www.fishersci.com/shop/products/bd-difco-dehydrated-culture-media-isp-medium-2/df0770179> (Year: 1969).*
International Search Report for PCT/KR2019/017238 mailed on Mar. 17, 2020.
Timothy S. Magnuson et al., "Immunologic Relatedness of Extracellular Ligninases from the Actinomycetes Streptomyces viridosporus T7A and Streptornyces badius 252", Applied Biochernistry and Biotechnology, vol. 28, 1991.
Rajesh Kumar Munagantia et al., "Antimicrobial profile of Arthrobacter kerguelensis VL-RK 09 isolated from Mango orchards", Brazilian Journal of Microbiology, vol. 47, pp. 1030-1038, 2016.
European Search Report for EP19899662.1 issued on Sep. 20, 2022 from European patent office in a counterpart European patent application.

(Continued)

*Primary Examiner* — Manjunath N Rao
*Assistant Examiner* — Ciara A McKnight
(74) *Attorney, Agent, or Firm* — The PL Law Group, PLLC

(57) ABSTRACT

A method for controlling a plant disease according to an embodiment includes treating a plant part, a seed, or a soil with a composition including at least one amino acid selected from the group consisting of glutamic acid, proline, tryptophan, and a combination thereof as an effective component. A method for promoting growth of an effective microorganism or controlling a plant disease uses prebiotics. As the amino acids have an effect of significantly promoting the growth of effective microorganism and having sustained maintenance of the effective microorganism at the same time and can reduce the incidence rate of plant disease, they can enhance the usefulness of eco-friendly microbial strains for disease control and be advantageously used as a substitute for chemical control agents.

3 Claims, 5 Drawing Sheets

Specification includes a Sequence Listing.

(56) References Cited

OTHER PUBLICATIONS

Anonymus, "Biolog Phenotype MicroArrays. Instructions for use", Sep. 1, 2002, XP055960233, URL:http://ecomicro.univ-lyonl.fr/IMG/pdf/ PM_resume.pdf.

Bochner Barry R, "Grobal phenotypic characterization of bacteria", FEMS Microbiology Reviews, vol. 33, No. 1,Jan. 1, 2009, pp. 191-205, XP055959365, DOI: 10.IIII/j.1574-6976.2008.00149.x.

Zeier Jurgen, "New insights into the regulation of plant immunity by amino acid metabolic pathways:Amino acid metabolism and plant immunity", Plant Cell and Environment, vol. 36, No. 12, May 17, 2013, pp. 2085-2103, XP055959106, GB ISSN: 0140-7791, DOI: 10.1111/pce.12122.

Kurth Florence et al., "*Streptomyces*-Induced Resistance Against Oak Powdery Mildew Involves Host Plant Responses in Defense, Photosynthesis, and Secondary Metabolism Pathways", Molecular Plant-Microbe Interactions, vol. 27, No. 9,Sep. 1, 2014, pp. 891-900, XP055959568, ISSN: 0894-0282, DOI: 10.1094/MPMI-10-13-0296-R.

Office action issued on Mar. 29, 2024 from China Patent Office in a counterpart China Patent Application No. 201980079611.0 (all the cited references are listed in this IDS.) (English translation is also submitted herewith.).

Zhen Wen-chao et al., "Study on determination and allelopathy of amino acids in strawberry root exudates and decomposing products", Journal of Agricultural University of Hebei, Mar. 2004, vol. 27, No. 2, pp. 76-80 (English Abstract is included in the first page.).

* cited by examiner

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
gtacggatct gcaccacga                    19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
aacagggtct ccacatcgac                   20

COMPOSITION FOR PROMOTING GROWTH OF EFFECTIVE MICROORGANISM AND CONTROLLING PLANT DISEASE USING PREBIOTICS, AND USE THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/017238, filed Dec. 6, 2019, which claims priority to the benefit of Korean Patent Application Nos. 10-2018-0166923 filed on Dec. 21, 2018 and 10-2019-0131906 filed Oct. 23, 2019 on in the Korean Intellectual Property Office, the entire contents of which are incorporated herein by reference.

BACKGROUND

1. Technical Field

The present invention relates to a composition for promoting growth of effective microorganism and controlling plant disease using prebiotics and use thereof.

2. Background Art

Gray mold is a major plant disease which causes tremendous economic damage to various crops including fruits and vegetables both before and after harvest, and it is found all over the world. The fungus causing gray mold, i.e., *Botrytis cinerea*, occurs in any part of crops such as leaf, stem, flower, fruit, and root, and it is particularly harmful to the crops cultivated in greenhouse facilities. Due to the characteristic of the fungus that it causes gray mold while leading saprophytic life at the same time, it induces secondary inflammation of old tissues or tissues which are affected by wound or other disease. By forming a *sclerotium* as a resistant body, the gray mold fungus can survive even in the presence of chemical pesticides and also in many unsuitable environments. It can even maintain the pathogenicity in soil and debris of dead plants for many years. Because the gray mold fungus can grow even at low temperature like 4° C., if proper air ventilation is not made in winter greenhouse facilities due to the temperature drop during night time, huge outbreak of gray mold may be yielded as a result of the low-temperature and high-humidity condition. Furthermore, being prone to genetic mutation, it is relatively easy for the gray mold fungus to obtain the resistance against chemical agents. Consequently, the great difficulty lies in controlling the gray mold fungus.

After initial outbreak, it is difficult to control blossom blight in strawberry as it rapidly spreads by wind, honey bee, or the like. In addition, flower germination is interfered by the blight to yield deformed fruits. In particular, the fungus causing blossom blight in strawberry (i.e., *Cladosporium cladosporioides*) has optimum temperature of 20 to 25° C. and a high tendency of occurring in a greenhouse with high humidity and condensation or an environment with poor sunlight, and it can grow even over dead plant, soil, organic matters, and the like. At present, the only method for controlling blossom blight in strawberry is to reduce the humidity in greenhouse and to treat, before blooming period, the plants with eco-friendly materials that are listed to be effective for controlling anthrax or chemical agents having little effect on pollen germination, or the like, as a preventive measure. As such, an agent for direct control of the fungus causing blossom blight in strawberry is in need so that a particular attention is made on development of an eco-friendly pesticide that is free of a problem like residual toxicity and environment contamination.

Wilt is a plant disease caused by *Fusarium oxysporum*, a pathogenic fungus, and it occurs all over the world including Europe, USA, Japan, and Brazil as well as South Korea. When the pathogenic fungus is densely present in soil as it has survived for a long period of time, a plant is infected via vessels and roots so that the symptom may be exhibited from all parts of the plant.

The prebiotics selected in the present invention are unharmful amino acids which are present in human body and natural environment, and it was found in the laboratory that they have an effect of promoting growth of effective microorganism. It was also found that, as a result of the treatment with prebiotics which are selected in the present invention, an effect of lowering the incidence rate of gray mold and bloom blight is obtained from crops cultivated in field and also higher density of effective microorganism and induction of sustained maintenance of the effective microorganism are obtained. Based on those effects, it was able to recognize the possibility of using the amino acids for improving the usefulness of an Eco-friendly microbial strains for controlling plant disease and also their use as a substitute for chemical control agent.

Meanwhile, in Korean Patent Registration No. 1626387, "Composition for controlling soil disease using new materials" is disclosed and "Composition for enhancing plant disease control effect of monosaccharides" is disclosed in Korean Patent Publication No. 2015-0126666. However, so far there is no disclosure of a "composition for promoting growth of effective microorganism and controlling plant disease using prebiotics".

SUMMARY

The present invention is devised under the circumstances that are described in the above. Specifically, it is found in the present invention that, when *Streptomyces badius* SP6C4 (also known as *Streptomyces globisporus* SP6C4) strain as an effective microorganism is treated with each of 5 kinds of amino acids (glutamic acid, proline, tryptophan, asparagine, and alanine), enhanced growth rate of SP6C4 strain is obtained from the group treated with 3 kinds of the amino acids (glutamic acid, proline, and tryptophan). As a result of examining the incidence rate of gray mold and bloom blight in strawberry by using 3 kinds of the amino acids which have been finally selected as described, it was found that lower incidence rate of gray mold and bloom blight in strawberry is obtained according to a treatment with 3 kinds of the amino acids compared to a control group which has not been treated with any amino acid. The incidence rate of gray mold and bloom blight in strawberry is significantly lower in the group treated with glutamic acid, in particular. It was also found that, when a plant is inoculated with wilt pathogen after tomato seeds are coated with glutamic acid or plant rhizosphere is treated first with glutamic acid, an excellent wilt control effect is obtained, and thus the present invention is completed accordingly.

To solve the problems described above, the present invention provides a composition for promoting growth of effective microorganism containing amino acids as an effective component.

The present invention further provides a composition for controlling plant disease containing one or more amino acids selected from the group consisting of glutamic acid, proline, and tryptophan as an effective component.

The present invention still further provides a method for controlling plant disease including treating a plant part, a seed, or soil with an effective amount of the aforementioned composition.

As the amino acids of the present invention with an activity of prebiotics have an effect of significantly promoting growth of effective microorganism and having sustained maintenance of the effective microorganism at the same time and can also significantly reduce the incidence rate of plant disease, they can be used for improving the usefulness of an eco-friendly microbial strain for controlling plant disease and also as a substitute for chemical control agent.

DETAILED DESCRIPTION

Figure 1:
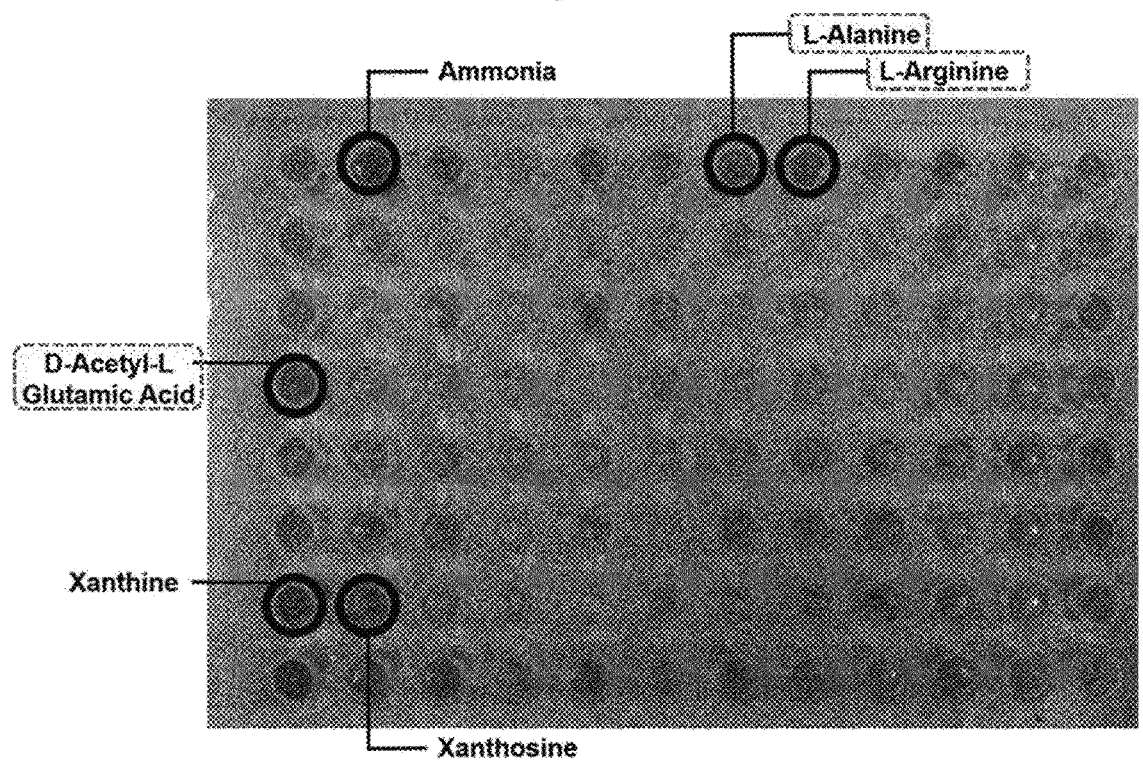
FIG. 1 shows the result of determining preference of *Streptomyces badius* SP6C4 strain, which has deposit number of KCCM11703P, for amino acids as prebiotics.

To achieve the purpose of the present invention, the present invention provides a composition for promoting growth of effective microorganism containing amino acids as an effective component.

As described herein, the amino acids have an activity of prebiotics, and the term "prebiotics" indicates a substance which is used to provide suitable and selected nutrients to a certain microorganism so that the colonization ability, reproduction ability, or the like of the microorganism can be enhanced, while all substances that are encompassed by the term "prebiotics" do not necessarily have the same characteristics.

With regard to the composition for promoting growth of effective microorganism according to one embodiment of the present invention, the amino acids may be one or more selected from the group consisting of glutamic acid, proline, and tryptophan, but they are not limited thereto.

Furthermore, the effective microorganism may be *Streptomyces badius* strain, and preferably *Streptomyces badius* SP6C4 strain with deposit number of KCCM11703P, but it is not limited thereto. *Streptomyces badius* SP6C4 strain is characterized by having a control effect against strawberry mold caused by *Cladosporium cladosporioides* (Korean Patent Registration No. 1695918).

The present invention further provides a composition for controlling plant disease containing one or more amino acids selected from the group consisting of glutamic acid, proline, and tryptophan as an effective component.

The composition for controlling plant disease according to one embodiment of the present invention may further contain effective microorganism or a culture broth thereof.

With regard to the composition for controlling plant disease according to one embodiment of the present invention, the effective microorganism may be *Streptomyces badius* strain, and preferably *Streptomyces badius* SP6C4 strain with deposit number of KCCM11703P, but it is not limited thereto. The aforementioned *Streptomyces badius* SP6C4 strain was duly deposited with Korean Culture Center of Microorganisms (KCCM) (having the address of KCCM, 3F Yurim B/D, 361-221, Hongje-1-dong, Sudaemun-gu, Seoul 120-091, Republic of Korea) under the Access number of KCCM11703P on Jun. 3, 2015. The deposit has been made under the terms of the Budapest Treaty and all restrictions imposed by the depositor on the availability to the public of the biological material will be irrevocably removed upon the granting of a patent.

Furthermore, the plant disease may be one or more selected from the group consisting of gray mold, bloom blight in strawberry, and wilt disease, but it is not limited thereto.

The composition for controlling plant disease according to the present invention may be produced, for example, as a solution that can be directly sprayed, powder or suspension form, highly concentrated aqueous, oily or other suspension, dispersion, emulsion, oil dispersion, paste, dust, sprinkle material, or granule formulation, but it is not limited thereto.

The composition for controlling plant disease according to the present invention may be formulated in various forms. The formulation can be prepared by adding a solvent and/or a carrier within a range in which the activity of the amino acids of the present invention is not inhibited by them. The formulation is often admixed with an inactive additive and a surface-active material, for example, an emulsifier or a dispersion agent. Examples of the suitable surface-active material can be an alkali metal, an alkaline earth metal salt, or an ammonium salt of aromatic sulfonic acid (e.g., lignosulfonic acid, phenol-sulfonic acid, naphthalene- and dibutyl naphthalene sulfonic acid), fatty acid, alkyl- and alkylaryl sulfonate, alkyl lauryl ether, or fatty alcohol sulfate, a salt of sulfated hexa-, hepta- and octadecanol, or fatty alcohol glycol ether, a condensate of naphthalene sulfonate or derivatives thereof and formaldehyde, a condensate of naphthalene or naphthalene sulfonate, phenol and formaldehyde, a condensate of polyoxyethylene octyl phenol, ethoxylated isooctyl-, octyl- or nonyl phenol, alkyl phenyl or tributyl phenyl polyglycol ether, alkylaryl polyether alcohol, isotridecyl alcohol, fatty alcohol/ethylene oxide, ethoxylated castor oil, polyoxyethylene alkyl ether or polyoxypropylene, lauryl alcohol polyglycol ether acetate, sorbitol ester, ligninsulfide waste liquid or methyl cellulose, but it is not limited thereto.

The suitable solid carrier material is, in principle, all porous, and it can be an agriculturally acceptable carrier, for example, mineral soils (e.g., silica, silica gel, silicate, talc, kaolinite, lime stone, lime, chalk, loess, clay, dolomite stone, diatomaceous earth, calcium sulfate, magnesium sulfate, magnesium oxide, and pulverized synthetic materials), fertilizer (ammonium sulfate, ammonium phosphate, ammonium nitrate, and urea), plant products (e.g., grain powder, tree bark powder, wood meal, and nut shell powder), or cellulose powder, but it is not limited thereto. Furthermore, the solid carrier may be used either singly or as a mixture of two or more kinds thereof.

The composition for controlling plant disease according to the present invention may be used for irrigation, foliar spray, seed sterilization, or sterilization of farming tools, but it is not limited thereto.

To enhance the absorption into a plant and the effect, the composition for controlling plant disease according to the present invention can be also used after being mixed with a diffusing agent and a permeating agent, or a surfactant.

The present invention still further provides a method for controlling plant disease including treating a plant part, a seed, or soil with an effective amount of the composition described above.

The method for controlling plant disease can be carried out by spraying and applying an effective amount of the composition for controlling plant disease of the present invention, which contains amino acids as an effective component, to a plant part, a seed, or soil, or immersing a plant part, a seed, or soil in the composition for controlling plant disease, but it is not limited thereto. The effective microorganism may be *Streptomyces badius* strain, and preferably *Streptomyces badius* SP6C4 strain with deposit number of KCCM11703P, but it is not limited thereto.

With regard to the method for controlling plant disease according to one embodiment of the present invention, when glutamic acid is the effective component, it may be preferable to have a plant seed coated with 15 to 25% (w/v) glutamic acid, or have a plant part treated with 1 to 3% (w/v) glutamic acid, but the method is not limited thereto.

Furthermore, the plant disease may be one or more selected from the group consisting of gray mold, bloom blight in strawberry, and wilt, but it is not limited thereto.

As described herein, the term "effective amount" indicates an amount that is sufficient to have a beneficial or desired effect. To control plant disease, the composition for control may be diluted homogeneously in water and applied to a plant or a cultivation field by using a suitable spraying device such as power sprayer.

Hereinbelow, the present invention is explained in greater detail in view of the Examples. However, the following Examples are given only for specific explanation of the present invention and it would be evident to a person who has common knowledge in the pertinent art that the scope of the present invention is not limited by them.

EXAMPLES

Example 1. First Selection of Effective Microorganism Regarding Amino Acid Preference Single colony of *Streptomyces badius* SP6C4 strain with deposit number of KCCM11703P was inoculated by streaking on MS medium (containing 20 g of mannitol, 20 g of soya, and 20 g of agar in 1 liter distilled water) and cultured for 7 days at 28° C. Upon the completion of culture to exhibit the production of full spores, 1 mL of sterile water was aliquoted to the medium and the spores were collected by scratching with sterile cotton wool followed by filtration using 15 mL syringe. Thus-completed spore stock was diluted in sterile water, and, after adjusting the concentration to $OD_{595}$ of 0.2±0.02, carrageenan stock (0.2% carrageenan and 50 mL distilled water) was prepared. The spore stock (1.5 mL) was admixed with 0.2% carrageenan stock (13.5 mL) and then the mixture (100 μl) was aliquoted onto a biolog plate (PM3B MICROPLATE™ Nitrogen Sources) followed by sealing the plate with a transparent film sheet. After 72 hours at 28° C., Redox dye mix MA (Biolog, Hayward, CA) was aliquoted to each well (10 μl per well) and sealed with a transparent film and a wrap to block the incorporation of $CO_2$ from outside. Culture was carried out at 37° C. for 24 hours and 48 hours, respectively. Finally, after carrying out vortexing for 10 seconds, a color change was observed with a naked eye over 6 hours with an interval of 1 hour. Determination was made based on the assumption that stronger purple color corresponds to higher growth of the microorganism. As a result, among the 95 kinds of amino acids, alanine, arginine, and glutamic acid were selected as a component which exhibits the darkest purple color and has no toxicity for plant, human and livestock (FIG. 1).

Figure 2:
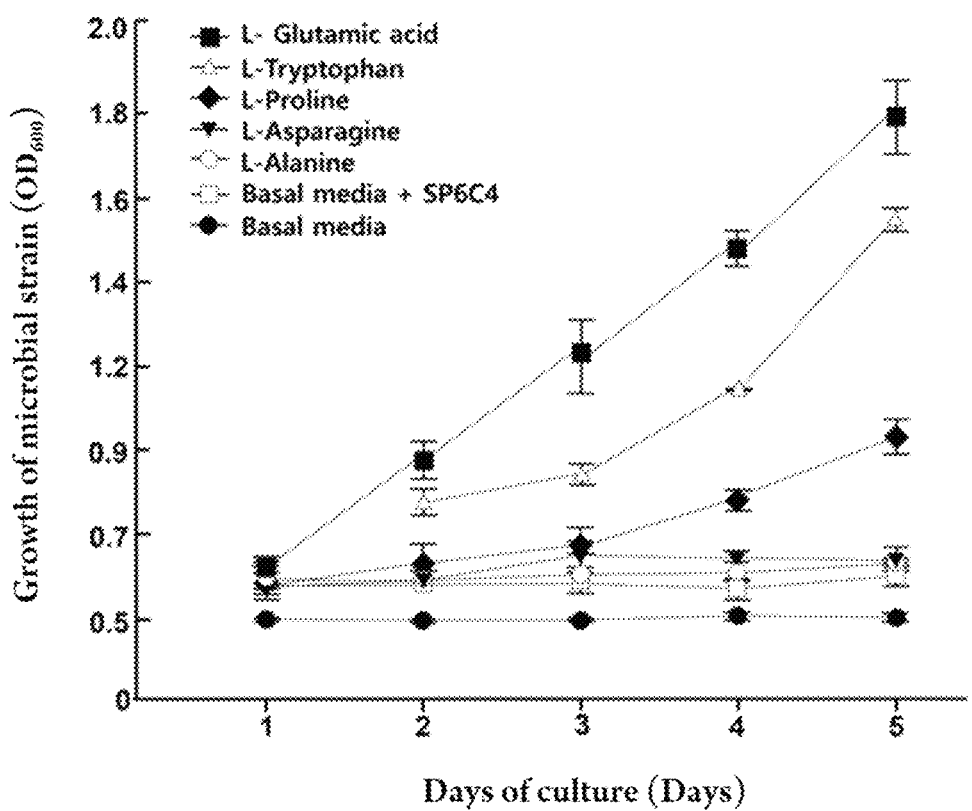
FIG. 2 shows the result of comparing the effect of promoting growth of *Streptomyces badius* SP6C4 strain as an effective microorganism in which the amino acids selected first with confirmed prebiotics activity (i.e., glutamic acid and alanine) and the amino acids that are previously known to have prebiotics activity (tryptophan, proline, and asparagine) are employed as a test subject.

Example 2. Determination of Effect of Promoting Growth of Effective Microorganism by the Amino Acids that are Selected First as Prebiotics Among the amino acids which have been found to have high preference based on the results of Example 1 above, including alanine and glutamic acid without any toxicity, by using tryptophan previously known to exhibit the effect of promoting spore forming of *Streptomyces* strain, proline exhibiting the effect of promoting growth and reducing the stress upon treatment on plant, asparagine known to control pH which affects the survival of *Streptomyces* strain, and basal medium as a control, the effect of promoting growth of microbial strain was examined again. To 10 μl of a spore stock of *Streptomyces badius* SP6C4 strain ($10^5$ cfu/mL), 80 μl of sterile water was added. After mixing with 10 μl of amino acids at concentration of 2%, the strain was cultured in a shaking incubator at a condition of 28° C. Growth of SP6C4 strain was examined by $OD_{600}$ for 5 days with an interval of 24 hours. As a result of determining the growth of SP6C5 strain on the fifth day of culture, it was found that $OD_{600}$ is 0.5 when the culture is carried out by adding only the basal medium as a control. However, when the culture is carried out by adding glutamic acid, tryptophan, or proline, $OD_{600}$ was between 0.9 and 1.8, showing a significant increase in the proliferation of SP6C4 strain. In case of the group treated with glutamic acid, in particular, final $OD_{600}$ value was 1.8 while showing continuous proliferation of the strain, thus exhibiting the highest proliferation effect (FIG. 2).

Example 3. Determination of Inhibitory Activity on Incidence Rate of Gray Mold and Bloom Blight by 3 Kinds of Amino Acids that are Selected as Prebiotics Based on a strawberry field test in which a treatment with amino acids (glutamic acid, proline, and tryptophan) as a test group or asparagine as a negative control is carried out, the effect exhibited on the incidence rate of gray mold and bloom blight was examined. Specifically, the test was carried out with an interval of 2 weeks during the cultivation period of strawberry. Length of 5M was set as a single section and foliar application was performed for three sections. For each section, 100 strawberries were randomly selected and incidence rate of the disease was determined.

Figure 3:
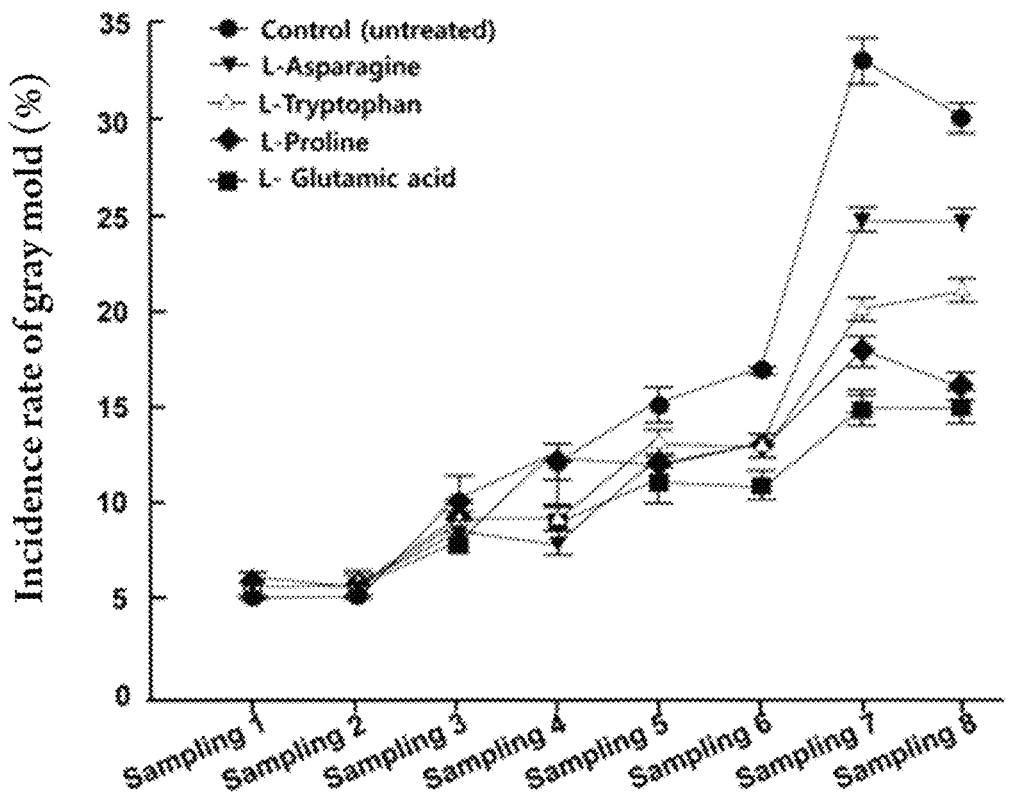
FIG. 3 shows the inhibitory effect on gray mold by a treatment with 3 kinds of the amino acids (glutamic acid, tryptophan, and proline) which have been selected through a strawberry field test.

As a treatment process, each amino acid was diluted to concentration of 2% in 15 liter distilled water, and the mixture (5 liter) was applied to each section. The treatment was carried out 8 times with an interval of 2 weeks. As the result is illustrated in FIG. 3, for gray mold, the incidence rate of 35% was shown from the non-treatment group (i.e., control) during the period of 8 treatments while the incidence rate of about 25% was shown from the asparagine treatment group as a negative control. On the contrary, it was shown that the incidence rate has decreased in order of glutamic acid, proline, and tryptophan as a test group. From the glutamic acid treatment group, in particular, the lowest incidence rate of less than 15% was shown (FIG. 3).

Figure 4:
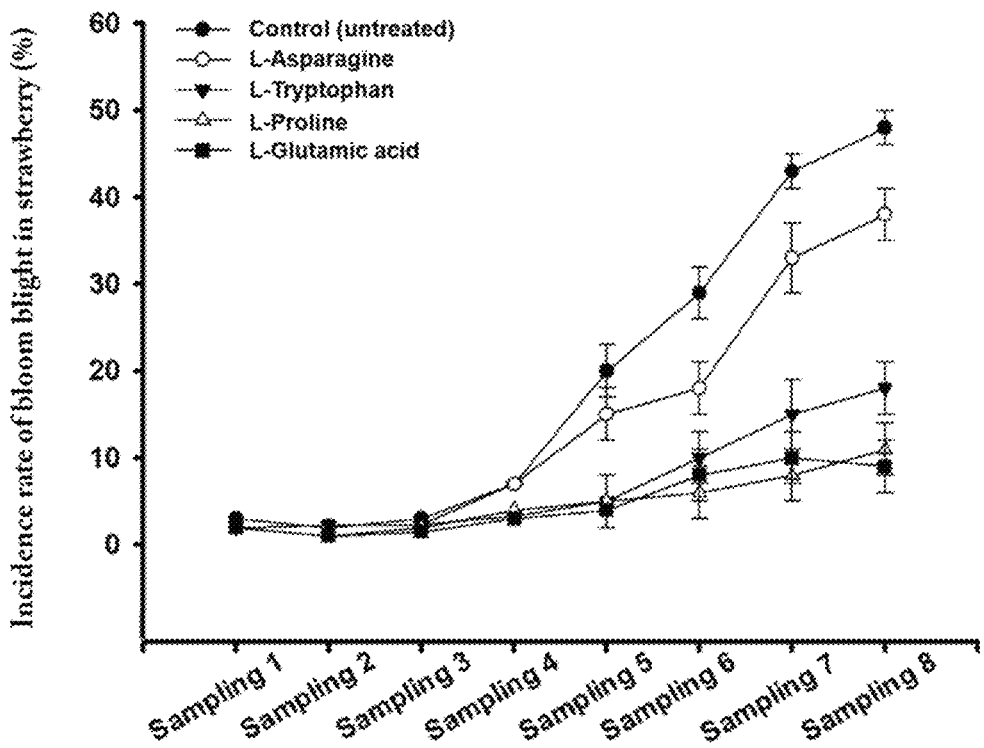
FIG. 4 shows the inhibitory effect on bloom blight by a treatment with 3 kinds of the amino acids (glutamic acid, tryptophan, and proline) which have been selected through a strawberry field test.

In addition, the test for controlling bloom blight disease was carried out with the same treatment groups and repetition number of test as the above gray mold test. As a result, the highest incidence rate up to 50% was shown from the non-treatment group (i.e., control) followed by the incidence rate up to about 40% from the asparagine treatment group. On the contrary, it was shown from the tryptophan, proline and glutamic acid treatment groups that the incidence rate is less than about 20%. From the glutamic acid treatment group, in particular, the incidence rate of about 10% was shown, indicating significantly decreased incidence rate of bloom blight compared to the non-treatment group (FIG. 4).

Figure 5:
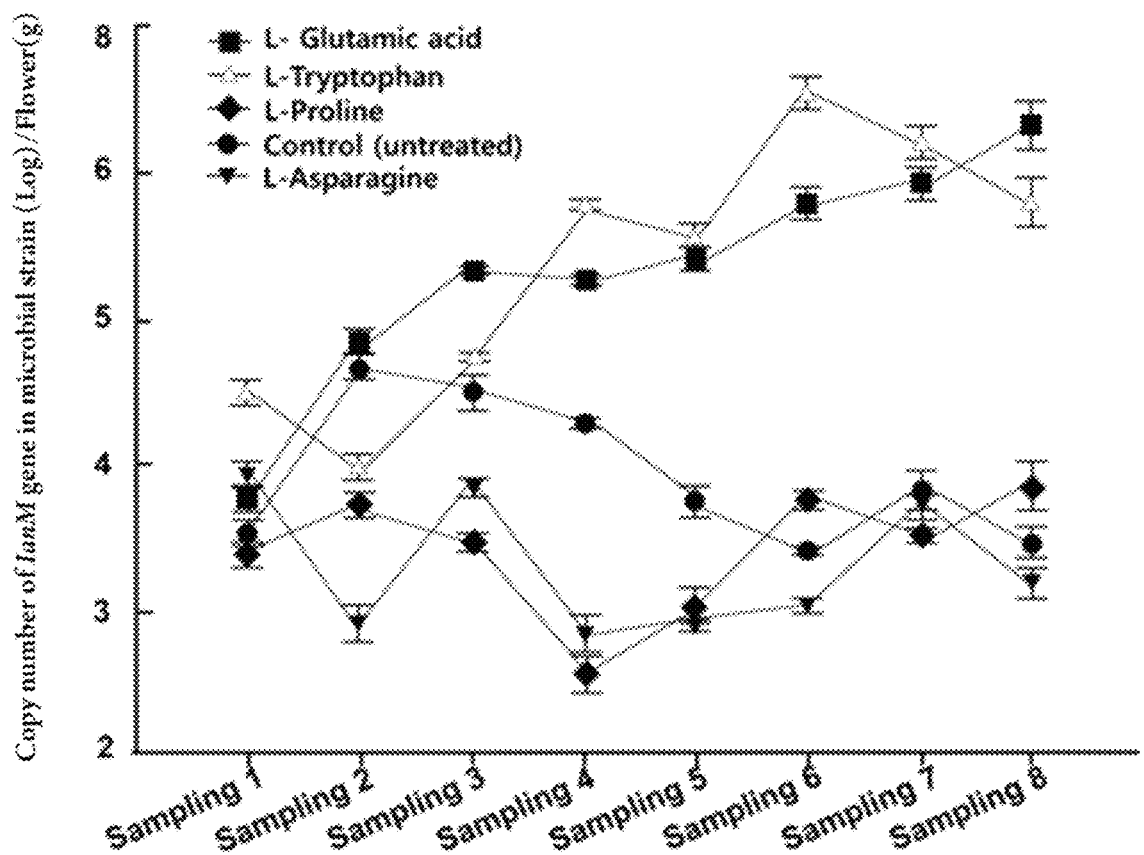
FIG. 5 shows the result of determining the effect of maintaining density of *Streptomyces badius* SP6C4 strain after a treatment with 3 kinds of the amino acids (glutamic acid, tryptophan, and proline) which have been selected through a strawberry field test.

Example 4. Determination of Sustained Maintenance of Density of Effective Microorganism after Treatment of 3 Kinds of Amino Acids that are Selected as Prebiotics To determine whether or not the density of effective microorganism is maintained even after a treatment of the amino acids, three strawberry flowers were collected, 3 times repeatedly, in each treatment period during which the test of inhibiting gray mold by the strawberry field test of Example 3 is carried out. After transfer to the lab under cold storage, 3 flowers were added to 30 mL of 1×PBS buffer and subjected to an ultrasonication treatment for 10 minutes. 3 mL of the supernatant was centrifuged for 10 minutes at a rate of 13,000 rpm, 1 mL of the resulting supernatant was discarded, and the pellet was dissolved in the remaining supernatant (2 mL). 500 µl of the mixture was admixed with 500 µl CTAB buffer followed by DNA purification. Each DNA was subjected to qPCR (quantitative polymerase chain reaction) by using lanM gene specific primers of *Streptomyces badius* SP6C4 strain (forward direction: 5'-gtacggatctgcaccacga-3' (SEQ ID NO: 1), reverse direction: 5'-aacagggtctccacatcgac-3' (SEQ ID NO: 2)). As the result is illustrated in FIG. 5, it was found that, in the glutamic acid treatment group, the microorganism concentration is continuously maintained at concentration of $10^5$ cfu/mL or higher except the first treatment out of 8 treatments.

Figure 6:
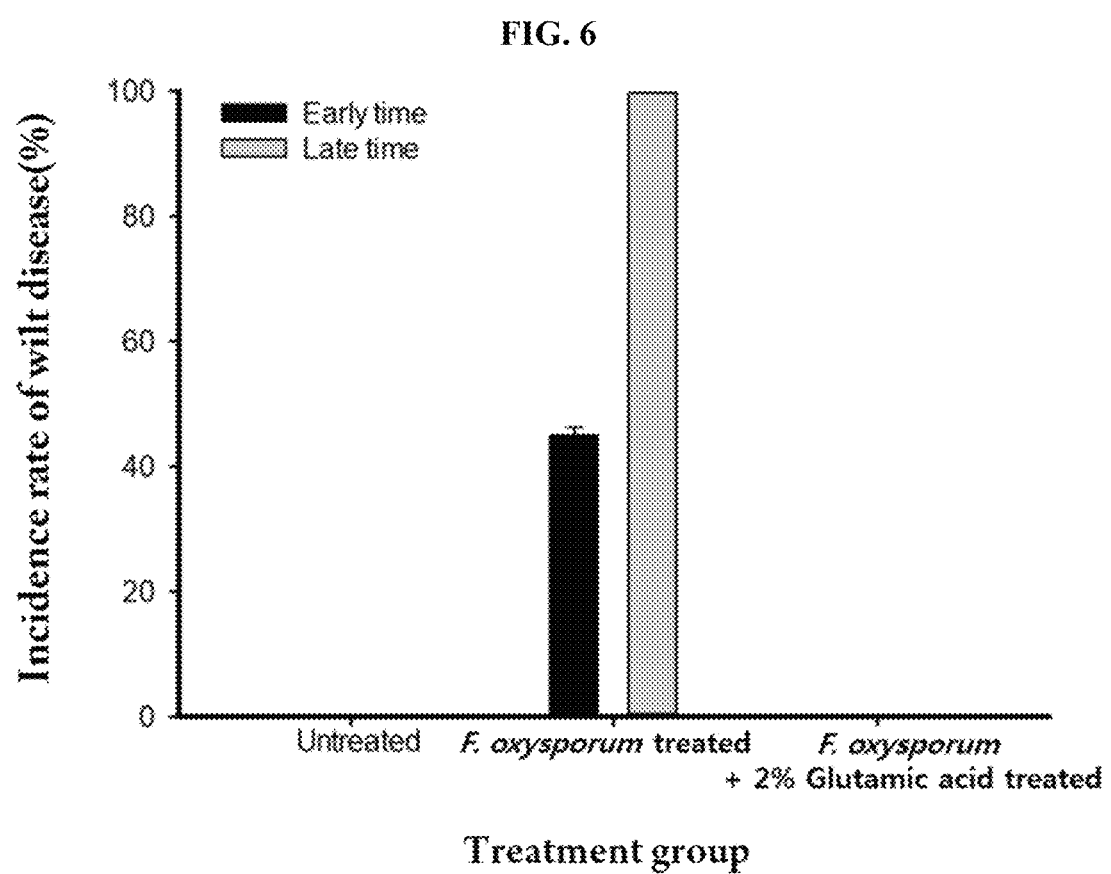
FIG. 6 shows the inhibitory effect on initial incidence of wilt disease when tomato seeds are coated with glutamic acid.

Example 5. Determination of Wilt Disease Controlling Activity after Coating Plant Seed with Glutamic Acid Selected as Prebiotics By using a concentrate of glutamic acid (20% (w/v)) and a concentrate of CMC (carboxyl methyl cellulose) (1% (w/v)) as a spreader, a mixture solution was prepared such that they have concentration of 2% and 0.1%, respectively. Forty to fifty tomato seeds of which surfaces have been sterilized with 70% (v/v) ethanol and 1% (v/v) sodium hypochlorite were added to 1 mL of the mixture solution and dried for 12 hours in a sterile bench at room temperature condition. After that, the coated seeds were planted to a square pot (3 cm×3 cm), 1 to 2 seeds per pot. *Fusarium oxysporum* spores as wilt pathogen were added in an amount of 3 mL with concentration of $10^5 \times 1.0$ CFU/mL. The treatment group obtained after completing pathogen inoculation to the seeds was transferred to a plant growth chamber which is set at 28° C. for 16 hours of light period and 25° C. for 8 hours of dark period. On Day 3 (Early time) and Day 10 (Late time) after transfer to a plant growth chamber, the incidence rate of wilt disease was examined. As a control, a non-treatment group and a group treated only with the pathogen were examined, each repeated 10 times. As the result is illustrated in FIG. 6, the group treated only with the pathogen showed the wilt disease incidence rate of about 50% at Early time, and the wilt incidence rate of 100% was shown from the same group after Day 10 (Late time). On the contrary, it was shown that wilt disease does not occur in the non-treatment group and also in the group which has been treated with both the glutamic acid and pathogen. It was found based on this result that, according to a treatment of seeds with glutamic acid selected as prebiotics, initial occurrence of wilt disease can be effectively inhibited.

Figure 7:
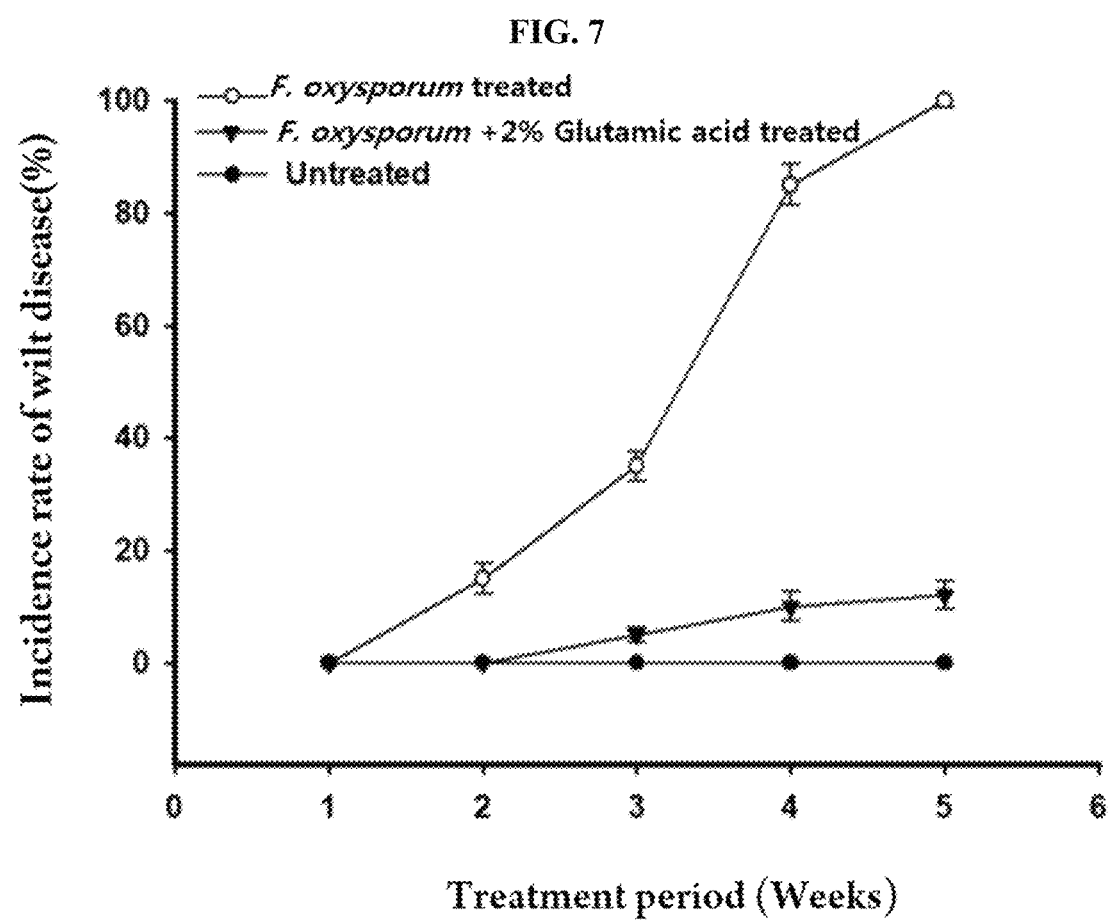
FIG. 7 shows the inhibitory effect on incidence of wilt disease when the rhizosphere of a tomato plant is treated first with glutamic acid and then treated with *Fusarium oxysporum* as a wilt pathogen.

Example 6. Determination of Wilt Disease Controlling Activity According to Treatment of Underground Part of Plant with Glutamic Acid To a tomato plant grown to have aboveground part of 8 to 10 cm, 2% glutamic acid solution was applied 2 times, in an amount of 20 mL with an interval of 5 days. Furthermore, by using a hemocytometer, chlamydospores in a suspension of the wilt pathogen, which has been prepared as a source of soil inoculation, were observed to find that the spore concentration is $10^{5-6} \times 1.0$ CFU/mL. A wound was created, by using a 5 mL tip, on the underground part of plant which has been treated twice with glutamic acid for 10 days, and then the spore suspension (10 mL) was applied to a pot with diameter of 9 cm. The plant inoculated with the pathogen was transferred to a plant growth chamber which is set at 28° C. for 16 hours of light period and 25° C. for 8 hours of dark period. Then, the incidence rate of disease was determined with an interval of 1 week. As a control, a group treated only with the pathogen and a plant not treated with any were tested, each repeated 5 times. As the result is illustrated in FIG. 7, for 2 weeks after the initial pathogen treatment, no significant difference in the incidence rate of disease was observed between the pathogen treatment group, non-treatment group, and group treated with both the pathogen and glutamic acid. However, from the week 4, the pathogen treatment group showed the incidence rate of 100% while the non-treatment group showed the incidence rate of 0% and the group treated with both the pathogen and glutamic acid showed the incidence rate of less than 15%. Based on this result, it was recognized that an occurrence of wilt disease can be effectively inhibited by firstly treating plant rhizosphere with glutamic acid.

A sequence listing electronically submitted with the present application on Jun. 8, 2021 as an ASCII text file named 20210608_Q53721GR08_TU_SEQ, created on May 20, 2021 and having a size of 1,000 bytes, is incorporated herein by reference in its entirety.

What is claimed is:

1. A method for controlling a plant disease, the method comprising:
    treating a plant part, a seed, or a soil with a composition comprising at least one amino acid selected from the group consisting of glutamic acid, proline, tryptophan, and a combination thereof as an effective component,
    wherein the plant disease is one or more selected from the group consisting of gray mold, bloom blight in strawberry, and wilt disease,
    wherein the composition further comprises a microorganism or a culture broth thereof,
    wherein the microorganism comprises *Streptomyces badius* SP6C4 strain deposited under Accession Number KCCM11703P.

2. A method for promoting a growth of a microorganism for a plant, the method comprising:
    treating a plant part, a seed, or a soil with a composition comprising an amino acid as an effective component to culture the microorganism in the presence of the composition,
    wherein the microorganism comprises *Streptomyces badius* SP6C4 strain deposited under Accession Number KCCM11703P.

3. The method of claim 2, wherein the amino acid is at least one selected from the group consisting of glutamic acid, proline, tryptophan, and a combination thereof.

* * * * *